United States Patent
Lee et al.

(10) Patent No.: US 10,208,325 B2
(45) Date of Patent: Feb. 19, 2019

(54) MICROORGANISM HAVING IMPROVED L-LYSINE PRODUCTIVITY AND METHOD FOR PRODUCING L-LYSINE USING SAME

(71) Applicant: CJ Cheiljedang Corporation, Seoul (KR)

(72) Inventors: Peter Lee, Gyeonggi-do (KR); Jun Ok Moon, Gyeonggi-do (KR); Hyung Joon Kim, Seoul (KR); Song Gi Ryu, Gyeonggi-do (KR)

(73) Assignee: CJ CHEILJEDANG CORPORATION (KR)

( * ) Notice: Subject to any disclaimer, the term of this patent is extended or adjusted under 35 U.S.C. 154(b) by 0 days.

(21) Appl. No.: 15/309,387

(22) PCT Filed: May 8, 2015

(86) PCT No.: PCT/KR2015/004588
§ 371 (c)(1),
(2) Date: Nov. 7, 2016

(87) PCT Pub. No.: WO2015/170907
PCT Pub. Date: Nov. 12, 2015

(65) Prior Publication Data
US 2017/0204439 A1    Jul. 20, 2017

(30) Foreign Application Priority Data

May 8, 2014   (KR) .................. 10-2014-0055102

(51) Int. Cl.
| | |
|---|---|
| C12P 13/08 | (2006.01) |
| C07K 14/34 | (2006.01) |
| C12N 9/16 | (2006.01) |
| C12R 1/15 | (2006.01) |

(52) U.S. Cl.
CPC .............. *C12P 13/08* (2013.01); *C07K 14/34* (2013.01); *C12N 9/16* (2013.01); *C12R 1/15* (2013.01)

(58) Field of Classification Search
CPC .............. C12P 13/08; C12R 1/15; C12N 9/16
See application file for complete search history.

(56) References Cited

U.S. PATENT DOCUMENTS

| | | | | |
|---|---|---|---|---|
| 6,962,989 B1 * | 11/2005 | Pompejus | .............. | C07H 21/02 530/350 |
| 7,332,310 B2 * | 2/2008 | Nakagawa | .............. | C07K 14/34 435/115 |

FOREIGN PATENT DOCUMENTS

| | | | | |
|---|---|---|---|---|
| EP | 2107128 B1 * | 10/2012 | .............. | C12Q 1/68 |
| JP | 2002-191370 A | 7/2002 | | |
| KR | 10-0789270 B1 | 1/2008 | | |
| KR | 10-0838035 B1 | 6/2008 | | |
| KR | 10-0838038 B1 | 6/2008 | | |
| KR | 10-1285945 B1 | 7/2013 | | |
| WO | WO2004-029193 A1 | 4/2004 | | |
| WO | WO2011-158975 A1 | 12/2011 | | |

OTHER PUBLICATIONS

European Search Report from EP 15789069.0 dated Nov. 15, 2017.
Brand S. et al. (2003) Arch Microbiol 180:33-44, "Identification and functional analysis of six mycoltltransferase genes of Corynebacterium glutamicum ATCC 13032: the genes cop1, cmt1, and cmt2 can replace each other in the synthesis of trehalose dicorynomycolate, a component of the mycolic acid layer of the cell envelope".
Kalinowski J. et al., (2003) Journal of Biotechnology 104:5-25, "The complete Corynebacterium glutamicum ATCC 13032 genome sequence and its impact on the production of L-aspartate-derived amino acids and vitamins".
Wendisch V. F. et al., (2006) Current Opinion in Microbiology, 9:268-274, "Metabolic engineering of *Escherichia coli* and Corynebacterium glutamicum for biotechnological production of organic acids and amino acids".

* cited by examiner

*Primary Examiner* — Ganapathirama Raghu
(74) *Attorney, Agent, or Firm* — Adsero IP

(57) ABSTRACT

Provided are a microorganism of the genus *Corynebacterium* having an enhanced activity to produce L-lysine as a result of inactivating a secretory protein and a method for producing L-lysine using the microorganism.

4 Claims, No Drawings

Specification includes a Sequence Listing.

MICROORGANISM HAVING IMPROVED L-LYSINE PRODUCTIVITY AND METHOD FOR PRODUCING L-LYSINE USING SAME

RELATED APPLICATIONS

This application is a National Stage Entry of International Application No. PCT/KR2015/004588, filed on May 8, 2015, and claims the benefit of Korean Application No. 10-2014-0055102, filed on May 8, 2014, which is hereby incorporated by reference in its entirety for all purposes as if fully set forth herein.

TECHNICAL FIELD

The present disclosure relates to a microorganism having enhanced ability to produce L-lysine and a method for producing L-lysine using the same.

Incorporated by reference herein in its entirety is the Sequence Listing entitled "sequence Listing.txt", created Nov. 1, 2016, size of 13 kilobytes.

BACKGROUND ART

L-lysine is used in the animal feed, human drug and cosmetic industries, and is produced by fermentation using a microorganism of the genus *Corynebacterium* or the genus *Escherichia*. In recent years, studies on the development of highly efficient production strains and fermentation process techniques have been conducted.

Many studies have been conducted to control foaming during fermentation of yeasts which are used in beer and wine production, and in recent studies, genes (AWA1, FPG1, and CFG1) having an effect on foaming have been identified (Shimoi H. et al., 2002, Appl. Environ. Microbiol. 68:2018-25; Blasco L. et al., Yeast. 2011, 28:437-51; Blasco L. et al., J. Agric. Food Chem. 2012, 60:10796-07). Herein, it was found that, in the case of a strain with these genes inactivated, foaming significantly decreased compared to that in the case of a parent strain, whereas in the case of a strain that overexpress these genes, foaming increased.

Foaming during culture of yeast occurs through a series of processes as follows. First, mannoprotein mixes with fine gas bubbles generated during fermentation. At this time, the inside of the gas bubbles becomes hydrophobic, and the outside of the gas bubbles becomes hydrophilic. For this reason, the viscosity of the culture medium is increased so that not only various proteins, but also cells mix, resulting in foaming (Swart C W. et al., FEMS Yeast Res. 2012, 12:867-69).

In beer production using yeast, a suitable level of foaming is required, but in fermentation of microorganisms that are used to produce large amounts of useful products such as amino acids, the inhibition of foaming is required. If an excessively large amount of foam is generated during culture, the viscosity of the culture medium will be increased, and thus the oxygen transfer rate (OTR) in the culture medium will decrease, and in severe cases, lysis of the cells will occur. The use of a large amount of an anti-foaming agent for inhibiting foaming can increase production costs in industrial terms and can have an adverse effect on cell growth.

Accordingly, the present inventors have screened genes of a microorganism of the genus *Corynebacterium*, which have an effect on a large amount of foaming, and have found that, when such genes are inactivated, foaming is effectively controlled so that an ability to produce L-lysine of the strain is increased, thereby completing the present disclosure.

DISCLOSURE

Technical Problem

It is an object of the present disclosure to provide a microorganism of the genus *Corynebacterium* having an enhanced abilitly to produce L-lysine.

Another object of the present disclosure is to provide a method for producing L-lysine using the microorganism of the genus *Corynebacterium*.

Technical Solution

In order to accomplish the above objects, one aspect of the present disclosure provides a microorganism of the genus *Corynebacterium* wherein at least one secretory protein selected from the group consisting of amino acid sequences of SEQ ID NOs: 1, 7 and 13 is inactivated.

Another aspect of the present disclosure provides a method of producing L-lysine by culturing a microorganism of the genus *Corynebacterium*.

Advantageous Effects

The microorganism according to the present disclosure is a microorganism wherein secretory proteins which are involved in foaming are inactivated so that an ability to produce L-lysine of the strain is increased. When this strain is used, foaming is reduced, it can be cultured without having to increase or without having to add a large amount of an anti-foaming agent, and the an ability to produce L-lysine of the strain can be increased. In addition, in industrial terms, effects such as the convenience of production and a reduction in the production cost can be obtained, and L-lysine can be efficiently produced.

MODE FOR INVENTION

Hereinafter, the present disclosure will be described in detail.

In one aspect, the present disclosure provides a microorganism of the genus *Corynebacterium* wherein at least one secretory protein having an amino acid sequence selected from the group consisting of amino acid sequences of SEQ ID NOs: 1, 7 and 13 is inactivated. If an excessively large amount of foam is generated during mass culture for producing L-lysine, the viscosity of the culture medium will be increased so that the oxygen transfer rate (OTR) in the culture medium will decrease, and in severe cases, lysis of the cells will also occur. In other words, it was thought that inactivating secretory proteins, which cause foaming, in terms of controlling foaming, would be advantageous for the production of lysine.

Thus, in an embodiment of the present disclosure, in order to improve a fermentation process for producing L-lysine and to screen major secretory proteins which cause foaming unnecessary for lysine production, *Corynebacterium glutamicum* KCCM11016P (this microorganism was disclosed as KFCC10881, and re-deposited with an International Depositary Authority under the Budapest Treaty under accession No. KCCM11016P; Korean Patent No. 10-0159812) was cultured, and then foam produced during the fermentation process was isolated, thereby obtaining peptides. The obtained peptides were analyzed, and three proteins detected in the largest amounts were selected, thereby selecting peptides encoded by genes of NCBI accession Nos. NCgl0336, NCgl0717 and NCgl2912 for *Corynebacterium glutamicum* ATCC13032.

In the present disclosure, the peptide encoded by the NCgl0336 gene is an esterase endogenously existing in the *Corynebacterium glutamicum*. Specifically, the peptide may have an amino acid sequence of SEQ ID NO: 1, and a protein having an amino acid sequence having a homology of at least 80%, specifically at least 90%, more specifically at least 95%, particularly specifically at least 97%, to the amino acid sequence of SEQ ID NO: 1, is also included in the scope of the secretory protein according to the present disclosure, as long as it is a protein having esterase activity. However, the secretory protein that is used in the present disclosure is not limited thereto, because the amino acid sequence of the protein showing esterase activity may differ depending on the species or strain of microorganisms. In addition, it is obvious that a protein having an amino acid sequence comprising a deletion, modification, substitution or deletion of one or several amino acids at one or more positions of the amino acid sequence of SEQ ID NO: 1 is also included in the scope of the present disclosure, as long as it has a sequence having homology to the sequence of SEQ ID NO: 1 and has biological activity substantially equal or similar to that of the protein having the amino acid sequence of SEQ ID NO: 1.

In the present disclosure, the NCgl0336 gene has a nucleotide sequence of SEQ ID NO: 2, and a nucleotide sequence having a homology of at least 80%, specifically at least 90%, more specifically 95%, particularly specifically 97%, to the nucleotide sequence of SEQ ID NO: 2, is also included in the scope of the present disclosure. In addition, variants of the sequence, which encode the same amino acid due to genetic code degeneracy, are also included in the scope of the present disclosure. Furthermore, a polynucleotide encoding NCgl0336 according to the present disclosure may be a variant encoding NCgl0336, which can hybridize to the nucleotide sequence of SEQ ID NO: 2 or a probe derived from the nucleotide sequence under stringent conditions and which normally functions.

In the present disclosure, the peptide encoded by the NCgl0717 gene is an esterase endogenously existing in the *Corynebacterium glutamicum*. Specifically, the peptide may have an amino acid sequence of SEQ ID NO: 7, and a protein having an amino acid sequence having a homology of at least 80%, specifically at least 90%, more specifically at least 95%, particularly specifically at least 97%, to the amino acid sequence of SEQ ID NO: 7, is also included in the scope of the secretory protein according to the present disclosure, as long as it is a protein having esterase activity. However, the secretory protein that is used in the present disclosure is not limited thereto, because the amino acid sequence of the protein showing esterase activity may differ depending on the species or strain of microorganisms. In addition, it is obvious that a protein having an amino acid sequence comprising a deletion, modification, substitution or deletion of one or several amino acids at one or more positions of the amino acid sequence of SEQ ID NO: 7 is also included in the scope of the present disclosure, as long as it has a sequence having homology to the sequence of SEQ ID NO: 7 and has biological activity substantially equal or similar to that of the protein having the amino acid sequence of SEQ ID NO: 7.

In the present disclosure, the NCgl0717 gene has a nucleotide sequence of SEQ ID NO: 8, and a nucleotide sequence having a homology of at least 80%, specifically at least 90%, more specifically 95%, particularly specifically 97%, to the nucleotide sequence of SEQ ID NO: 8, is also included in the scope of the present disclosure. In addition, variants of the sequence, which encode the same amino acid due to genetic code degeneracy, are also included in the scope of the present disclosure. Furthermore, a polynucleotide encoding NCgl0717 according to the present disclosure may be a variant encoding NCgl0717, which can hybridize to the nucleotide sequence of SEQ ID NO: 8 or a probe derived from the nucleotide sequence under stringent conditions and which normally functions.

In the present disclosure, the peptide encoded by the NCgl2912 gene is an esterase endogenously existing in the *Corynebacterium glutamicum*. Specifically, the peptide may have an amino acid sequence of SEQ ID NO: 13, and a protein having an amino acid sequence having a homology of at least 80%, specifically at least 90%, more specifically at least 95%, particularly specifically at least 97%, to the amino acid sequence of SEQ ID NO: 13, is also included in the scope of the secretory protein according to the present disclosure, as long as it is a protein having esterase activity. However, the secretory protein that is used in the present disclosure is not limited thereto, because the amino acid sequence of the protein showing esterase activity may differ depending on the species or strain of microorganisms. In addition, it is obvious that a protein having an amino acid sequence comprising a deletion, modification, substitution or deletion of one or several amino acids at one or more positions of the amino acid sequence of SEQ ID NO: 13 is also included in the scope of the present disclosure, as long as it has a sequence having homology to the sequence of SEQ ID NO: 13 and has biological activity substantially equal or similar to that of the protein having the amino acid sequence of SEQ ID NO: 13.

In the present disclosure, the NCgl2912 gene has a nucleotide sequence of SEQ ID NO: 14, and a nucleotide sequence having a homology of at least 80%, specifically at least 90%, more specifically 95%, particularly specifically 97%, to the nucleotide sequence of SEQ ID NO: 14, is also included in the scope of the present disclosure. In addition, variants of the sequence, which encode the same amino acid due to genetic code degeneracy, are also included in the scope of the present disclosure. Furthermore, a polynucleotide encoding NCgl2912 according to the present disclosure may be a variant encoding NCgl2912, which can hybridize to the nucleotide sequence of SEQ ID NO: 14 or a probe derived from the nucleotide sequence under stringent conditions and which normally functions.

As used herein, the term "homology" refers to identity to a given amino acid sequence or nucleotide sequence and may be expressed as percentage. In the specification, a homologous sequence having activity equal or similar to a given amino acid sequence or nucleotide sequence is expressed as "% homology". The homology of the amino acid sequence can be determined by using, for example, algorithm BLAST (see Karlin and Altschul, Pro. Natl. Acad. Sci. USA, 90, 5873 (1993)) or FASTA by Pearson (see Methods Enzymol., 183, 63 (1990)). Programs called BLASTN and BLASTX have been developed on the basis of this algorithm BLAST (see www.ncbi.nlm.nih.gov).

As used herein, the term "stringent conditions" means conditions which permit specific hybridization between polynucleotides. For example, Such stringent conditions are described in detail in J. Sambrook et al., Molecular Cloning, A Laboratory Manual, 2nd Edition, Cold Spring Harbor Laboratory press, Cold Spring Harbor, New York, 1989; F.

M. Ausubel et al., Current Protocols in Molecular Biology, John Wiley & Sons, Inc., New York.

As used herein, "inactivation" may be achieved by any inactivation method known in the art. In the present disclosure, "inactivation" means that the expression of an endogenous gene is reduced compared to that in a wild-type strain, or the gene is not expressed, or the gene has no activity or reduced activity even though it is expressed. The activation may be achieved by mutating all or part of the nucleotide sequence or all or part of the expression regulatory sequence thereof by deletion, substitution, insertion, or a combination thereof.

As a specific example, a microorganism with the endogenous gene inactivated may be prepared by transforming a microorganism of the genus Corynebacterium with a recombinant vector comprising a gene fragment obtained by deleting the open reading frame of the endogenous gene, thereby deleting or mutating the endogenous gene. Insertion of the gene into the chromosome can be performed by any method known in the art.

As used herein, the term "endogenous" enzyme and activity refers to an enzyme present originally in a microorganism or a cell and the activity of the enzyme. Namely, the term means an enzyme and its activity before the enzyme and activity are modified.

As used herein, the term "recombinant vector" refers to a DNA construct containing the nucleotide sequence of a target protein-encoding gene operably linked to a suitable regulatory sequence so as to be able to express the target gene in a suitable host cell. The regulatory sequence includes a promoter capable of initiating transcription, any operator for regulating this transcription, a sequence encoding a suitable mRNA ribosome binding site, and a sequence for regulating the termination of transcription and translation. Once transformed into a suitable host, the vector may replicate or function independently of the host genome, or may integrate into the genome itself. The vector that is used in the present disclosure is not specifically limited and may be any vector known in the art, as long as it can replicate in a host.

Examples of the vector that is used in construction of the recombinant vector include natural or recombinant plasmids, cosmids, viruses, and bacteriophages. For example, the phage vector or cosmid vector that is used in the present disclosure may be pWE15, M13, λMBL3, λMBL4, λIXII, λASHII, λAPII, λt10, λt11, Charon4A, Charon21A or the like, and the plasmid vector that is used in the present disclosure may be pDZ type, pBR type, pUC type, pBluescriptII type, pGEM type, pTZ type, pCL type, pET type or the like. A vector that may be used in the present disclosure is not specifically limited, and any known expression may be used in the present disclosure.

As used herein, the term "transformation" means introducing a vector comprising a polynucleotide encoding a target protein into a host cell so as to be able to express a protein encoded by the polynucleotide in the host cell. The introduced polynucleotide may be inserted and located in the chromosome of the host cell or located outside the chromosome, as long as it can be expressed in the host cell. In addition, the polynucleotides include DNA and RNA, which encode the target protein. As long as the polynucleotide can be introduced in the host cell and expressed therein, it may be introduced in any form. For example, the polynucleotide can be introduced into the host cell in the form of an expression cassette which is a polynucleotide construct including all elements required for self-expression. The expression cassette generally includes a promoter which is operably linked to the open reading frame (hereinafter abbreviated as "ORF") of the gene, a transcription termination signal, a ribosome binding site, and a translation termination signal. The expression cassette may be in the form of a self-replicable expression vector. In addition, the polynucleotide may be introduced into the host cell by itself and operably linked to the sequence necessary for expression in the host cell.

As a parent strain into which the recombinant vector is to be introduced, any microorganism having an ability to produce producing L-lysine may be used without limitation. Specifically, a microorganism of the genus Corynebacterium or the genus Brevibacterium may be used. More specifically, a Corynebacterium glutamicum microorganism may be used.

As used herein, the expression "microorganism having an ability to produce L-lysine" refers to a microorganism obtained by manipulating a generally known gene so as to be capable of producing L-lysine. For example, the microorganism may be a microorganism obtained either by inserting one or more genes selected from the group consisting of aspB (aspartate aminotransferase-encoding gene), lysC (aspartate kinase-encoding gene), asd (aspartate semialdehyde dehydrogenase-encoding gene), dapA (dihydrodipicolinate synthase-encoding gene), dapB (dihydrodipicolinate reductase-encoding gene) and lysA (diaminodipimelate decarboxylase-encoding gene), which are endogenous in a microorganism of the genus Corynebacterium and are involved in the production of L-amino acids, or by treating an L-leucine auxotrophic mutant strain with N-methyl-N'-nitro-N-nitrosoguanidine (NTG).

More specifically, a microorganism of the genus Corynebacterium used in the present disclosure are Corynebacterium glutamicum KCCM11016P (this microorganism was disclosed as KFCC10881, and re-deposited with an International Depositary Authority under the Budapest Treaty under accession No. KCCM11016P; Korean Patent No. 10-0159812), Corynebacterium glutamicum KCCM10770P (Korean Patent No. 10-0924065), Corynebacterium glutamicum L-lysine-producing strain KCCM11347P (this microorganism was disclosed as KFCC10750, and re-deposited with an International Depositary Authority under the Budapest Treaty under accession No. KCCM11347P; Korean Patent No. 10-0073610), and a Corynebacterium glutamicum CJ3P strain (Binder et al., Genome Biology 2012, 13:R40), but are not limited thereto.

In a preferred embodiment of the present disclosure, a microorganism transformed according to the present disclosure may be Corynebacterium glutamicum KCCM11502P, KCCM11481P or KCCM11482P.

In another aspect, the present disclosure also provides a method of producing L-lysine using the transformed microorganism. More specifically, the present disclosure provides a method for producing L-lysine, comprising the steps of: culturing the microorganism of the present disclosure to produce L-lysine in a culture or cell of the microorganism; and recovering L-lysine from the culture medium.

In the method of the present disclosure, culture of a microorganism of the genus Corynebacterium may be performed using any culture conditions and culture method known in the art.

For example, a medium that may be used for culture of a microorganism of the genus Corynebacterium is disclosed in Manual of Methods for General Bacteriology by the American Society for Bacteriology (Washington D.C., USA, 1981).

Sugar sources that may be used in the medium include sugars and carbohydrates such as glucose, saccharose, lactose, fructose, maltose, starch or cellulose; oils and fats such as soybean oil, sunflower oil, castor oil or coconut oil; fatty acids such as palmitic acid, stearic acid or linoleic acid; alcohols such as glycerol or ethanol; and organic acids such as acetic acid. These substances may be used individually or in a mixture.

Nitrogen sources which may be used include compounds containing organic nitrogen, such as peptone, yeast extract, meat extract, malt extract, corn steep liquor, soybean meal and urea, or inorganic compounds such as ammonium sulfate, ammonium chloride, ammonium phosphate, ammonium carbonate and ammonium nitrate. The nitrogen sources may also be used individually or as a mixture.

Phosphorus sources which may be used include potassium dihydrogen phosphate or dipotassium hydrogen phosphate or the corresponding sodium salts. The culture medium should furthermore contain metal salts such as magnesium sulfate or iron sulfate, which are required for growth. Finally, essential growth substances such as amino acids and vitamins may be used in addition to the above-mentioned substances. Moreover, suitable precursors may be added to the culture medium. Said substances may be added to the culture in a batch or a continuous manner by a suitable method during culturing.

The pH of the culture may be controlled by using basic compounds such as sodium hydroxide, potassium hydroxide, ammonia or aqueous ammonia or acidic compounds such as phosphoric acid or sulfuric acid in a suitable manner. Foaming can be controlled by using antifoaming agents such as fatty acid polyglycol esters. Aerobic conditions are maintained by introducing oxygen or oxygen-containing gas mixtures (e.g., air) into the culture. The culture temperature is usually from 20° C. to 45° C., specifically from 25° C. to 40° C. Culturing may be continued until a desired amount of L-lysine has been produced. Specifically, the culturing time is 10-160 hours.

In the method of the present disclosure, the culturing may be performed continuously or in a batch process or in a fed batch or repeated fed batch process. This culturing may be performed using any method well known in the art.

Hereinafter, the present disclosure will be described in further detail with reference to examples. It is to be understood, however, that these examples are for illustrative purposes only and are not intended to limit the scope of the present disclosure.

EXAMPLES

Example 1: Screening of Secretory Proteins Related to Foaming During Culture

In this Example, in order to screen secretory proteins that cause foaming, an experiment was performed in the following manner.

First, *Corynebacterium glutamicum* KCCM11016P (this microorganism was disclosed as KFCC10881, and re-deposited with an International Depositary Authority under the Budapest Treaty under accession No. KCCM11016P; Korean Patent No. 10-0159812) was cultured using a 1-L fermenter, and then only foam produced during the fermentation process was isolated and concentrated in a 15 ml test tube.

For identification of proteins contained in the concentrated foam sample, a suitable amount of a loading dye containing a surfactant was added to the sample which was then electrophoresed on 8% sodium dodecyl sulfate polyacrylamide gel. After electrophoresis, the sodium dodecyl sulfate polyacrylamide gel was stained by Coomassie blue staining. Then, the stained protein bands were excised and digested with trypsin to obtain peptides, and the amino acid sequences of the obtained peptides were analyzed by an LC-MS/MS method.

The analyzed peptides were identified by searching genes of a microorganism of the genus *Corynebacterium* using the Blast research provided by the National Center for Biotechnology Information (NCBI). Among the identified peptides, three proteins detected in the largest amounts were selected, thereby finally selecting genes encoding the proteins. The selected genes are NCBI accession Nos. NCgl0336, NCgl0717 and NCgl2912.

Example 2: Construction of Recombinant Plasmid for Inactivation of Secretory Protein NCgl0336 Gene For construction of a recombinant plasmid capable of inactivating the NCgl0336 gene on the *Corynebacterium* chromosome, the amino acid sequence (SEQ ID NO: 1) and nucleotide sequence (SEQ ID NO: 2) of NCgl0336 were obtained based on the nucleotide sequence deposited in the NIH Genbank. In order to prepare a gene fragment by deleting the open reading frame of NCgl0336, primers of SEQ ID NOs: 3 to 6 were constructed based on the sequence of SEQ ID NO: 2.

```
SEQ ID NO. 3:
5'-atcctctagagtcgacGAAGCCTCTGCACCTCGCTG-3';

SEQ ID NO. 4:
5'-TATAGTTCGGTTCCGCGTCTCCAACGCATCCGGCC-3';

SEQ ID NO. 5:
5'-CGGAACCGAACTATACCACCGAGGGACGCATTCTC-3';

SEQ ID NO. 6:
5'-atgcctgcaggtcgacGCTCAAACGCACGAGCGAAG-3'.
```

Using the genomic DNA of *Corynebacterium glutamicum* as a template, PCR was performed using a primer set of SEQ ID NO: 3 and SEQ ID NO: 4 and a primer set of SEQ ID NO: 5 and SEQ ID NO: 6 [Sambrook et al, Molecular Cloning, a Laboratory Manual (1989), Cold Spring Harbor Laboratories]. The PCR was performed for 30 cycles, each consisting of denaturation at 95° C. for 30 sec, annealing at 50° C. for 30 sec, and polymerization at 72° C. for 1 min.

As a result, NCgl0336-A and NCgl0336-B, which are DNA fragments comprising a 342-bp NCgl0336 gene fragment and a 315-bp NCgl0336 gene fragment, respectively, were obtained. The DNA fragment obtained by PCR amplification was ligated to a pDZ plasmid (Korean Patent No. 10-0924065) by use of an Infusion cloning kit (Invitrogen), and then transformed into *E. coli* DH5α and plated on an LB solid medium containing 25 mg/L of kanamycin. A colony transformed with a plasmid having the desired gene inserted therein was selected by PCR, and then the plasmid was isolated using a generally known plasmid extraction technique. The plasmid was named "pDZ-ΔNCgl0336". pDZ-ΔNCgl0336 is a plasmid wherein a 503-bp gene fragment of NCgl0336 was deleted.

Example 3: Construction of Recombinant Plasmid for Inactivation of Secretory Protein NCgl0717 Gene For construction of a recombinant plasmid capable of inactivating the NCgl0717 gene on the *Corynebacterium* chromosome, the amino acid sequence (SEQ ID NO: 7) and nucleotide sequence (SEQ ID NO: 8) of NCgl0717 were obtained based on the nucleotide sequence deposited in the NIH Genbank. In order to prepare a gene fragment by deleting the open reading frame of NCgl0717, primers of SEQ ID NOs: 9 to 12 were constructed based on the sequence of SEQ ID NO: 8.

```
SEQ ID NO. 9:
5'-CCGGGGATCCTCTAGAGTTCGCGGATAAATGGG-3';

SEQ ID NO. 10:
5'-CACGTGAAATTCAGGTCGCGTGGTTCACCTCCGAAG-3';

SEQ ID NO. 11:
5'-CTTCGGAGGTGAACCACGCGACCTGAATTTCACGTG-3';

SEQ ID NO. 12:
5'-GCAGGTCGACTCTAGAGGTCCCATGATTGTTCTG-3'.
```

Using the genomic DNA of *Corynebacterium glutamicum* as a template, PCR was performed using a primer set of SEQ ID NO: 9 and SEQ ID NO: 10 and a primer set of SEQ ID NO: 11 and SEQ ID NO: 12. The PCR was performed for 30 cycles, each consisting of denaturation at 95° C. for 30 sec, annealing at 50° C. for 30 sec, and polymerization at 72° C. for 1 min.

As a result, NCgl0717-A and NCgl0717-B, which are DNA fragments comprising a 493-bp NCgl0717 gene fragment and a 491-bp NCgl0717 gene fragment, respectively, were obtained. The DNA fragment obtained by PCR amplification was ligated to a pDZ plasmid by use of an Infusion cloning kit (Invitrogen), and then transformed into *E. coli* DH5α and plated on an LB solid medium containing 25 mg/L of kanamycin. A colony transformed with a plasmid having the desired gene inserted therein was selected by PCR, and then the plasmid was isolated using a generally known plasmid extraction technique. The plasmid was named "pDZ-ΔNCgl0717". pDZ-ΔNCgl0717 is a plasmid wherein a 786-bp gene fragment of NCgl0717 was deleted.

Example 4: Construction of Recombinant Plasmid for Inactivation of Secretory Protein NCgl2912 Gene For construction of a recombinant plasmid capable of inactivating the NCg2912 gene on the *Corynebacterium* chromosome, the amino acid sequence (SEQ ID NO: 13) and nucleotide sequence (SEQ ID NO: 14) of NCgl2912 were obtained based on the nucleotide sequence deposited in the NIH Genbank. In order to prepare a gene fragment by deleting the open reading frame of NCgl2912, primers of SEQ ID NOs: 15 to 18 were constructed based on the sequence of SEQ ID NO: 14.

```
SEQ ID NO. 15:
5'-CCGGGGATCCTCTAGAGCTGCAAGAAGTGCGAC-3';

SEQ ID NO. 16:
5'-CTCGTAGTCGCTAGCACCTATTACGGGAGGTC-3';

SEQ ID NO. 17:
5'-GACCTCCCGTAATAGGTGCTAGCGACTACGAG-3';

SEQ ID NO. 18:
5'-GCAGGTCGACTCTAGACCCGAGCTATCTAACAC-3'.
```

Using the genomic DNA of *Corynebacterium glutamicum* as a template, PCR was performed using a primer set of SEQ ID NO: 15 and SEQ ID NO: 16 and a primer set of SEQ ID NO: 17 and SEQ ID NO: 18. The PCR was performed for 30 cycles, each consisting of denaturation at 95° C. for 30 sec, annealing at 50° C. for 30 sec, and polymerization at 72° C. for 1 min.

As a result, NCgl2912-A and NCgl2912-B, which are DNA fragments comprising a 444-bp NCgl2912 gene fragment and a 636-bp NCgl2912 gene fragment, respectively, were obtained. The DNA fragment obtained by PCR amplification was ligated to a pDZ plasmid by use of an Infusion cloning kit (Invitrogen), and then transformed into *E. coli* DH5α and plated on an LB solid medium containing 25 mg/L of kanamycin. A colony transformed with a plasmid having the desired gene inserted therein was selected by PCR, and then the plasmid was isolated using a generally known plasmid extraction technique. The plasmid was named "pDZ-ΔNCgl2912". pDZ-ΔNCgl2912 is a plasmid wherein a 128-bp gene fragment of NCgl2912 was deleted.

Example 5: Construction and Evaluation of Secretory Protein Gene-Inactivated Strain from Lysine-Producing Strain KCCM11016P Each of the three recombinant plasmids (pDZ-ΔNCgl0336, pDZ-ΔNCgl0717 and pDZ-ΔNCgl2912) constructed in Examples 2, 3 and 4 was transformed into *Corynebacterium glutamicum* KCCM11016P by an electric pulse method, and strains wherein the target gene was inactivated by homologous recombination were prepared by a PCR method. The prepared strains were named "KCCM11016P-ΔNCgl0336", "KCCM11016P-ΔNCgl0717", and "KCCM11016P-ΔNCgl2912", respectively.

Each of the three strains and a control strain was inoculated in a 25-ml corner-baffled flask containing 25 ml of the following seed medium, and was cultured with shaking at 200 rpm and 30° C. for 20 hours. Next, 1 ml of the seed culture was inoculated in a 250-ml corner-baffled flask containing 24 ml of the following production medium, and was cultured with shaking at 200 rpm and 37° C. for 96 hours. The composition of each of the seed medium and the production medium is as follows.

Seed Medium (pH 7.0)

20 g of glucose, 10 g of $(NH_4)_2SO_4$, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium-pantothenate, and 2000 μg of nicotinamide (per liter of distilled water).

Production Medium (pH 7.0)

100 g of glucose, 40 g of $(NH_4)_2SO_4$, 2.5 g of soybean protein, 5 g of cornsteep solid, 3 g of urea, 1 g of $KH_2PO_4$, 0.5 g of $MgSO_4 \cdot 7H_2O$, 100 μg of biotin, 1000 μg of thiamine HCl, 2000 μg of calcium-pantothenate, 3000 μg of nicotinamide, and 30 g of $CaCO_3$ (per liter of distilled water).

After completion of the culturing process, the culture was transferred into a graduated cylinder, and the height of the produced foam in the culture was measured, and also the concentration of L-lysine in the culture was measured by HPLC. The results of the measurement are shown in Table 1 below. The results in Table 1 are the results of three repeated experiments, and L-lysine production was evaluated based on the average value.

TABLE 1

| | Lysine (g/L) | | | Foam (cm/L) | | |
|---|---|---|---|---|---|---|
| | Batch 1 | Batch2 | Batch 3 | Batch 1 | Batch 2 | Batch 3 |
| KCCM11016P | 43.5 | 43.1 | 43.4 | 4.5 | 5.0 | 4.7 |
| KCCM11016P-ΔNCgl0336 | 46.1 | 45.8 | 45.7 | 4.1 | 4.6 | 4.3 |
| KCCM11016P-ΔNCgl0717 | 45.9 | 46.4 | 46.1 | 3.9 | 4.4 | 4.0 |
| KCCM11016P-ΔNCgl2912 | 45.8 | 46.0 | 45.8 | 4.2 | 4.7 | 4.4 |

As shown in Table 1 above, the L-lysine production of the strain wherein each of the NCgl0336, NCgl0717 and NCgl2912 gene was inactivated increased about 6% compared to that of the parent strain KCCM11016P. In addition, foam in the culture of the strain wherein each of the NCgl0336, NCgl0717 and NCgl2912 gene was inactivated decreased about 6-15% compared to that in the culture of the parent strain.

Thus, it was found that, when the major secretory proteins of the Corynebacterium sp. microorganism, which are unnecessary for lysine production, are inactivated, the generation of foam during culture of the microorganism can be effectively controlled, thereby increasing L-lysine production.

Example 6: Construction and Evaluation of Secretory Protein-Inactivated Strains from L-Lysine-Producing Strain In order to examine whether the effects of inactivation of secretory proteins in the L-lysine-producing strain Corynebacterium glutamicum KCCM10770P (Korean Patent No. 10-0924065) having an enhanced lysine biosynthetic pathway are similar to the experimental results of Example 5, strains in which each of the three secretory proteins was inactivated were constructed in the same manner as described in Example 5. The constructed strains were named "KCCM10770P-ΔNCgl0336", "KCCM10770P-ΔNCgl0717", and "KCCM10770P-ΔNCgl2912". The amount of L-lysine production of each of the constructed strains together with the amount of foam generated was examined.

In order to examine the lysine production of the strains, each of the strains together with the control strain was cultured in the same manner as described in Example 5. After completion of culturing, the amount of foam generated was measured in the same manner as described in Example 5, and the concentration of L-lysine was measured by HPLC. The results of the measurement are shown in Table 2 below. The results in Table 2 are the results of three repeated experiments, and L-lysine production was evaluated based on the average value.

TABLE 2

| | Lysine (g/L) | | | Foam (cm/L) | | |
|---|---|---|---|---|---|---|
| | Batch 1 | Batch2 | Batch 3 | Batch 1 | Batch 2 | Batch 3 |
| KCCM10770P | 46.1 | 46 | 46.3 | 5.1 | 5.6 | 5.2 |
| KCCM10770P-ΔNCgl0336 | 47.9 | 48.2 | 47.7 | 4.6 | 4.9 | 4.5 |
| KCCM10770P-ΔNCgl0717 | 48.3 | 47.7 | 48.1 | 4.6 | 4.6 | 4.3 |
| KCCM10770P-ΔNCgl2912 | 47.9 | 48.5 | 48.2 | 4.9 | 5.4 | 5.0 |

As shown in Table 2 above, the lysine production of the strain wherein each of the NCgl0336, NCgl0717 and NCgl2912 gene was inactivated increased about 4% compared to that of the parent strain KCCM10770P. In addition, foam in the culture of the strain wherein each of the NCgl0336, NCgl0717 and NCgl2912 gene was inactivated decreased about 4-18% compared to that of the parent strain.

Thus, it was found that, when the major secretory proteins of Corynebacterium glutamicum KCCM10770P (Korean Patent No. 10-0924065), which are unnecessary for lysine production, are inactivated, the generation of foam during culture of the microorganisms can be effectively controlled, thereby increasing L-lysine production, similar to the results of Example 6.

Example 7: Construction and Evaluation of Secretory Protein-Inactivated Strains from L-Lysine-Producing Strain KCCM11347P In order to examine the effects of inactivation of secretory proteins in the L-lysine-producing strain Corynebacterium glutamicum KCCM11347P (this microorganism was disclosed as KFCC10750, and re-deposited with an International Depositary Authority under the Budapest Treaty under accession No. KCCM11347P; Korean Patent No. 10-0073610) constructed by artificial mutation, strains in which each of the three secretory proteins was inactivated were constructed in the same manner as described in Example 5 or 6. The constructed strains were named "KCCM11347P-ΔNCgl0336", "KCCM11347P-ΔNCgl0717", and "KCCM11347P-ΔNCgl2912". The amount of L-lysine production of each of the constructed strains together with the amount of foam generated was examined.

In order to examine the lysine production of the strains, each of the strains together with the control strain was cultured in the same manner as described in Example 5 or 6. After completion of culturing, the amount of foam generated was measured in the same manner as described in Example 5 or 6, and the concentration of L-lysine was measured by HPLC. The results of the measurement are shown in Table 3 below. The results in Table 3 are the results of three repeated experiments, and L-lysine production was evaluated based on the average value.

TABLE 3

| | Lysine (g/L) | | | Foam (cm/L) | | |
|---|---|---|---|---|---|---|
| | Batch 1 | Batch2 | Batch 3 | Batch 1 | Batch 2 | Batch 3 |
| KCCM11347P | 38.6 | 38.2 | 38.3 | 5.4 | 6.0 | 5.7 |
| KCCM11347P-ΔNCgl0336 | 40.1 | 40.2 | 40.1 | 5.1 | 5.1 | 5.3 |
| KCCM11347P-ΔNCgl0717 | 40.1 | 39.7 | 40.5 | 4.7 | 5.1 | 5.0 |
| KCCM11347P-ΔNCgl2912 | 39.8 | 40.3 | 40.3 | 5.1 | 5.6 | 5.4 |

As shown in Table 3 above, the lysine production of the strain wherein each of the NCgl0336, NCgl0717 and NCgl2912 gene was inactivated increased about 5% compared to that of the parent strain KCCM11347P. In addition, foam in the culture of the strain wherein each of the NCgl0336, NCgl0717 and NCgl2912 gene was inactivated decreased about 4-15% compared to that of the parent strain.

Thus, it was found that, when the major secretory proteins of Corynebacterium glutamicum KCCM11347P (Korean Patent No. 94-0001307), which are unnecessary for lysine production, are inactivated, the generation of foam during culture of the microorganisms can be effectively controlled, thereby increasing L-lysine production, similar to the results of Examples 5 and 6.

Example 8: Construction and Evaluation of Secretory Protein-Inactivated Strains from L-Lysine-Producing Strain CJ3P In order to examine the effects of inactivation of secretory proteins in *Corynebacterium glutamicum* CJ3P (Binder et al. Genome Biology 2012, 13:R40) having an ability to produce L-lysine, constructed by introducing three mutations [pyc (P458S), hom(V59A), and lysC(T311I)] into a wild-type strain, like Examples 5, 6 and 7, strains in which each of the three secretory proteins was inactivated were constructed in the same manner as described in Example 5, 6 or 7. The constructed strains were named "CJ3P-ΔNCg10336", "CJ3P-ΔNCg10717", and "CJ3P-ΔNCg12912". The amount of L-lysine production of each of the constructed strains together with the amount of foam generated was examined.

In order to examine the lysine production of the strains, each of the strains together with the control strain was cultured in the same manner as described in Example 5, 6 or 7. After completion of culturing, the amount of foam generated was measured in the same manner as described in Example 5, 6 or 7, and the concentration of L-lysine was measured by HPLC. The results of the measurement are shown in Table 4 below. The results in Table 4 are the results of three repeated experiments, and L-lysine production was evaluated based on the average value.

TABLE 4

|  | Lysine (g/L) | | | Foam (cm/L) | | |
| --- | --- | --- | --- | --- | --- | --- |
|  | Batch 1 | Batch2 | Batch 3 | Batch 1 | Batch 2 | Batch 3 |
| CJ3P | 7.9 | 8 | 8.1 | 8.7 | 9.1 | 8.6 |
| CJ3P-ΔNCg10336 | 8.5 | 8.6 | 8.8 | 7.8 | 8.3 | 7.9 |
| CJ3P-ΔNCg10717 | 8.4 | 8.5 | 8.7 | 7.7 | 7.5 | 7.2 |
| CJ3P-ΔNCg12912 | 8.7 | 8.6 | 8.6 | 8.4 | 8.6 | 8.2 |

As shown in Table 4 above, the lysine production of the strain wherein each of the NCg10336, NCg10717 and NCg12912 gene was inactivated increased about 8% compared to that of the parent strain CJ3P. In addition, foam in the culture of the strain wherein each of the NCg10336, NCg10717 and NCg12912 gene was inactivated decreased about 5-17% compared to that of the parent strain.

Thus, it was found that, when the major secretory proteins of *Corynebacterium glutamicum* CJ3P, which are unnecessary for lysine production, are inactivated, the generation of foam during culture of the microorganism can be effectively controlled, thereby increasing L-lysine production, similar to the results of Examples 5, 6 and 7.

Example 9: Construction and Evaluation of Secretory Protein-Inactivated Strains from L-Lysine-Producing Strain KCCM11016P In order to examine the effects of co-inactivation of secretory proteins in the L-lysine-producing strain *Corynebacterium glutamicum* KCCM11016P, three strains in which the secretory protein genes were co-inactivated were constructed in the same manner as described in Examples 5, 6, 7 and 8. The constructed strains in which a combination of the genes was inactivated were named "KCCM11016P-ΔNCg10336/ΔNCg10717", "KCCM11016P-ΔNCg10336/ΔNCg12912", and "KCCM11016P-ΔNCg10717/ΔNCg12912", and the amount of L-lysine production of each of the constructed strains together with the amount of foam generated was examined.

In order to compare the lysine production of the strains, each of the strains together with the control strain was cultured in the same manner as described in Example 5, 6, 7 or 8. After completion of culturing, the amount of foam generated was measured in the same manner as described in Example 5, 6, 7 or 8, and the concentration of L-lysine was measured by HPLC. The results of the measurement are shown in Table 5 below. The results in Table 5 are the results of three repeated experiments, and L-lysine production was evaluated based on the average value.

TABLE 5

|  | Lysine (g/L) | | | Foam (cm/L) | | |
| --- | --- | --- | --- | --- | --- | --- |
|  | Batch 1 | Batch2 | Batch 3 | Batch 1 | Batch 2 | Batch 3 |
| KCCM11016P | 43.3 | 43.1 | 43.4 | 4.6 | 4.9 | 4.7 |
| KCCM11016P-ΔNCg10336/ΔNCg10717 | 46.1 | 45.7 | 45.2 | 4.4 | 4 | 4.2 |
| KCCM11016P-ΔNCg10336/ΔNCg12912 | 45.5 | 45.9 | 46.1 | 4.2 | 4.3 | 4.4 |
| KCCM11016P-ΔNCg10717/ΔNCg12912 | 46 | 45.1 | 45.7 | 4 | 3.9 | 4.5 |

As shown in Table 5 above, the lysine production of the strain in which the NCg10336/NCg10717, NCg10336/NCg12912 or NCg10717/NCg12912 genes were co-inactivated increased about 5% compared to that of the parent strain KCCM11016P. In addition, foam in the culture of the strain in which the NCg10336/NCg10717, NCg10336/NCg12912 or NCg10717/NCg12912 genes were co-inactivated decreased about 10-14% compared to the parent strain.

Thus, it was found that, when the major secretory proteins of a microorganism of the genus *Corynebacterium*, which are unnecessary for lysine production, are inactivated, the generation of foam during culture of the microorganism can be effectively controlled, thereby increasing L-lysine production.

Example 10: Construction and Evaluation of Strain, in which all Secretory Proteins were Inactivated, from L-Lysine-Producing Strain KCCM11016P In order to examine the effects of inactivation of all secretory proteins in the L-lysine-producing strain *Corynebacterium glutamicum* KCCM11016P, a strain in which all the three secretory proteins were inactivated was constructed in the same manner as described in Example 5, 6, 7, 8 or 9. The strain was named "KCCM11016P-ΔNCg10336/ΔNCg10717/ΔNCg12912". The amount of L-lysine production of the constructed strain together with the amount of foam generated was examined.

In order to examine the lysine production of the strain, the strain together with the control strain was cultured in the same manner as described in Example 5, 6, 7, 8 or 9. After completion of culturing, the amount of foam generated was measured in the same manner as described in Example 5, 6, 7, 8 or 9, and the concentration of L-lysine was measured by HPLC. The results of the measurement are shown in Table 6 below. The results in Table 6 are the results of three repeated experiments, and L-lysine production was evaluated based on the average value.

TABLE 6

|  | Lysine (g/L) | | | Foam (cm/L) | | |
| --- | --- | --- | --- | --- | --- | --- |
|  | Batch 1 | Batch2 | Batch 3 | Batch 1 | Batch 2 | Batch 3 |
| KCCM11016P | 43.4 | 43.3 | 43.1 | 4.7 | 4.6 | 5.0 |
| KCCM11016P-ΔNCgl0336/ΔNCgl0717/ΔNCgl2912 | 46.4 | 46.3 | 46.7 | 3.9 | 4.1 | 3.8 |

As shown in Table 6 above, the L-lysine production of the strain in which the NCgl0336, NCgl0717 and NCgl2912 genes were all inactivated increased about 7% compared to that of the parent strain KCCM11016P. In addition, foam in the culture of the strain in which the NCgl0336, NCgl0717 and NCgl2912 genes were all inactivated decreased about 17% compared to that of the parent strain.

Thus, it was found that, when the major secretory proteins of a microorganism of the genus *Corynebacterium*, which are unnecessary for lysine production, are inactivated, the generation of foam during culture of the microorganism can be effectively controlled, thereby increasing L-lysine production.

From the above-described results, it was found that inactivation of the major secretory proteins in the L-lysine-producing strain has the effect of controlling foam which is overproduced during culture, thereby increasing an ability to produce L-lysine together with the growth of cells. The strains KCCM11016P-ΔNCgl0336, KCCM11016P-ΔNCgl0717 and KCCM11016P-ΔNCgl2912 were named "CA01-2281", "CA01-2279" and "CA01-2280", respectively. CA01-2279 and CA01-2280 were internationally deposited with the Korean Culture Center of Microorganisms on Nov. 22, 2013 under accession numbers KCCM11481P (CA01-2279) and KCCM11482P (CA01-2280), respectively, and CA01-2281 was internationally deposited with the Korean Culture Center of Microorganisms on Dec. 13, 2013 under accession number KCCM11502P (CA01-2281).

Accession Numbers
Depository authority: Korean Culture Center of Microorganisms;
Accession number: KCCM11481P;
Deposit date: Nov. 22, 2013.
Depository authority: Korean Culture Center of Microorganisms;
Accession number: KCCM11482P;
Deposit date: Nov. 22, 2013.
Depository authority: Korean Culture Center of Microorganisms;
Accession number: KCCM11502P;
Deposit date: Dec. 13, 2013.

| Applicant's or agent's file reference PP15-0104 | International application No. |
|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page 18, line 1. | |
|---|---|
| B. IDENTIFICATION OF DEPOSIT | Further deposits are identified on an additional sheet ☐ |
| Name of depositary institution<br>Korean Culture Center of Microorganisms | |
| Address of depositary institution *(including postal code and country)*<br>Yurim B/D, 45 Hongjenae 2ga-gil, Seodaemun-gu, Seoul 120-861, Republic of Korea | |
| Date of deposit<br>November 22, 2013 | Accession Number<br>KCCM11481P |
| C. ADDITIONAL INDICATIONS *(leave blank if not applicable)*     This information is continued on an additional sheet ☐ | |
| D. DESIGNATED STATES FOR WHICH INDICATIONS ARE MADE *(if the indications are not for all designated States)* | |
| E. SEPARATE FURNISHING OF INDICATIONS *(leave blank if not applicable)* | |
| The indications listed below will be submitted to the International Bureau later *(specify the general nature of the indications e.g., "Accession Number of Deposit")* | |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July1998; reprint January 2004)

| Applicant's or agent's file reference PP15-0104 | International application No. |
|---|---|
| | |

INDICATIONS RELATING TO DEPOSITED MICROORGANISM OR OTHER BIOLOGICAL MATERIAL (PCT Rule 13bis)

| A. The indications made below relate to the deposited microorganism or other biological material referred to in the description on page 19, line 1. ||
|---|---|
| B. IDENTIFICATION OF DEPOSIT | Further deposits are identified on an additional sheet ☐ |
| Name of depositary institution Korean Culture Center of Microorganisms ||
| Address of depositary institution *(including postal code and country)* Yurim B/D, 45 Hongjenae 2ga-gil, Seodaemun-gu, Seoul 120-861, Republic of Korea ||
| Date of deposit November 22, 2013 | Accession Number KCCM11482P |
| C. ADDITIONAL INDICATIONS *(leave blank if not applicable)*     This information is continued on an additional sheet ☐ ||
| ||
| D. DESIGNATED STATES FOR WHICH INDICATIONS ARE MADE *(if the indications are not for all designated States)* ||
| ||
| E. SEPARATE FURNISHING OF INDICATIONS *(leave blank if not applicable)* ||
| The indications listed below will be submitted to the International Bureau later *(specify the general nature of the indications e.g., "Accession Number of Deposit")* ||

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July1998; reprint January 2004)

| Applicant's or agent's file reference PP15-0104 | International application No. |
|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page 20, line 1. | |
|---|---|
| B. IDENTIFICATION OF DEPOSIT | Further deposits are identified on an additional sheet ☐ |
| Name of depositary institution<br>Korean Culture Center of Microorganisms | |
| Address of depositary institution *(including postal code and country)*<br>Yurim B/D, 45 Hongjenae 2ga-gil, Seodaemun-gu, Seoul 120-861, Republic of Korea | |
| Date of deposit<br>December 13, 2013 | Accession Number<br>KCCM11502P |
| C. ADDITIONAL INDICATIONS *(leave blank if not applicable)*  This information is continued on an additional sheet ☐ | |
| | |
| D. DESIGNATED STATES FOR WHICH INDICATIONS ARE MADE *(if the indications are not for all designated States)* | |
| | |
| E. SEPARATE FURNISHING OF INDICATIONS *(leave blank if not applicable)* | |
| The indications listed below will be submitted to the International Bureau later *(specify the general nature of the indications e.g., "Accession Number of Deposit")* | |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July1998; reprint January 2004)

The invention claimed is:

1. A genus of *Corynebacterium* having an ability to produce L-lysine and comprising at least one inactivated secretory protein selected from the group consisting of amino acid sequences of SEQ ID NOs: 1, 7 and 13.

2. The L-lysine-producing microorganism according to claim 1, wherein the microorganism of the genus *Corynebacterium* is *Corynebacterium glutamicum*.

3. A method for producing L-lysine, comprising the steps of:
culturing the microorganism of claim 1 to produce L-lysine in culture medium or cell of the microorganism; and
recovering L-lysine from the culture medium or the cell.

4. A method for producing L-lysine, comprising the steps of:
culturing the microorganism of claim 2 to produce L-lysine in culture medium or cell of the microorganism; and
recovering L-lysine from the culture medium or the cell.

* * * * *

SEQUENCE LISTING

<160> NUMBER OF SEQ ID NOS: 18

<210> SEQ ID NO 1
<211> LENGTH: 365
<212> TYPE: PRT
<213> ORGANISM: Corynebacterium glutamicum
<220> FEATURE:
<221> NAME/KEY: PEPTIDE
<222> LOCATION: (1)..(365)
<223> OTHER INFORMATION: Esterase encoded by NCgl0336 gene

<400> SEQUENCE: 1

Met Lys Leu Leu Arg Arg Ile Ala Ala Pro Ala Ile Ala Leu Gly Ile
1               5                   10                  15

Ala Met Ser Thr Ile Val Thr Pro Ser Thr Ala Gly Ala Ala Glu Val
            20                  25                  30

Thr Pro Ala Asp Val Ala Gly Asp Thr Ala Leu Ser Thr Ile Ser Asp
        35                  40                  45

Ser Ala Pro Ala Asp Glu Ala Ser Ala Pro Arg Trp Arg Ala His Val
    50                  55                  60

Asn Ala Ala Asp Glu Arg Val Lys Glu Met Trp Ala Tyr Ser Pro Ser
65                  70                  75                  80

Met Asp Arg Asn Val Pro Leu Val Val Ile Thr Ala Asp Glu Ser Ala
                85                  90                  95

Gly Pro Arg Pro Val Ile Tyr Leu Leu Asn Gly Gly Asp Gly Gly Glu
            100                 105                 110

Gly Ala Ala Asn Trp Val Met Gln Thr Asp Val Leu Asp Phe Tyr Leu
        115                 120                 125

Glu Lys Asn Val Asn Val Val Ile Pro Met Glu Gly Lys Phe Ser Tyr
    130                 135                 140

Tyr Thr Asp Trp Val Glu Glu Asn Ala Ser Leu Gly Gly Lys Gln Met
145                 150                 155                 160

Trp Glu Thr Phe Leu Val Lys Glu Leu Pro Gly Pro Leu Glu Glu Lys
                165                 170                 175

Leu Asn Thr Asp Gly Gln Arg Ala Ile Ala Gly Met Ser Met Ser Ala
            180                 185                 190

Thr Thr Ser Leu Leu Phe Pro Gln His Phe Pro Gly Phe Tyr Asp Ala
        195                 200                 205

Ala Ala Ser Phe Ser Gly Cys Ala Ala Thr Ser Ser Leu Leu Pro Trp
    210                 215                 220

Glu Tyr Leu Lys Leu Thr Leu Asp Arg Gly Asn Ala Thr Pro Glu Gln
225                 230                 235                 240

Met Trp Gly Pro Arg Gly Gly Glu Tyr Asn Ile Tyr Asn Asp Ala Leu
                245                 250                 255

Ile Asn Ser Asp Lys Leu Arg Gly Thr Glu Leu Tyr Val Ser Asn Ala
            260                 265                 270

Ser Gly Leu Ala Gly Glu Trp Glu Ser Val Asp Ser Pro Arg Phe Glu
        275                 280                 285

Gly Leu Asn Gln Gln Val Gln Ser Ile Ala Met Ala Glu Thr Val Val
    290                 295                 300

Thr Gly Gly Ile Ile Glu Ala Ala Thr Asn Lys Cys Thr His Asp Leu
305                 310                 315                 320

Lys Ala Lys Leu Asp Ser Ala Gly Ile Pro Ala Asp Trp Asn Leu Arg
                325                 330                 335

Pro Thr Gly Thr His Ser Trp Gly Trp Trp Gln Asp Asp Leu Arg Gly
            340                 345                 350

Ser Trp Thr Thr Phe Ala Arg Ala Phe Glu Leu Glu Ala
        355                 360                 365

<210> SEQ ID NO 2
<211> LENGTH: 1098
<212> TYPE: DNA
<213> ORGANISM: Corynebacterium glutamicum
<220> FEATURE:
<221> NAME/KEY: gene
<222> LOCATION: (1)..(1098)
<223> OTHER INFORMATION: NCgl0336 gene

<400> SEQUENCE: 2

```
atgaagcttc ttcgccgcat cgctgcacca gccatcgcgc tgggaattgc gatgtccacc      60
attgtcacgc catccaccgc aggcgctgcc gaagtaaccc cagcagacgt tgctggcgat     120
actgcactat ccaccatctc cgatagtgct cctgcagatg aagcctctgc acctcgctgg     180
cgcgcacacg tcaacgcagc agacgagcgc gtcaaagaaa tgtgggcata ctccccttcc     240
atggaccgca atgtgccact ggtagttata actgccgatg agtccgcagg tcctcgtcct     300
gtgatttacc ttcttaacgg tggcgacggt ggcgaaggtg ccgctaactg ggttatgcag     360
actgacgttc tggatttcta cctagaaaag aacgttaacg ttgttattcc aatggaaggc     420
aagttttcct actacaccga ctgggtagaa gagaatgcgt ccctcggtgg caagcaaatg     480
tgggaaacct tcctggtgaa ggaacttcca ggaccattgg aagaaaagct caacactgac     540
ggtcagcgtg caattgctgg catgtccatg tccgcaacta cttccctact cttcccacaa     600
cacttcccag gcttctacga cgcagcagca tccttctcag gatgcgcagc aacctcaagc     660
ctgctcccat gggaataccc caaactcacc cttgaccgcg caacgcaac cccagaacaa     720
atgtggggac cacgtggtgg cgaatacaac atctacaacg acgcactgat caactccgac     780
aaactacgcg gaaccgaact atacgtctcc aacgcatccg gccttgctgg tgaatgggaa     840
tccgtcgaca gcccacgctt cgaaggactc aaccaacaag ttcagtccat cgcaatggca     900
gaaactgtgg taaccggcgg catcatcgaa gctgcaacca acaagtgcac ccacgacctc     960
aaggcaaaac ttgactccgc cggcatccca gccgactgga acctccgccc aaccggcacc    1020
cactcatggg gctggtggca agatgacctc cgcggatctt ggaccacctt cgctcgtgcg    1080
tttgagctag aggcctag                                                  1098
```

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3

```
atcctctaga gtcgacgaag cctctgcacc tcgctg                                36
```

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4

```
tatagttcgg ttccgcgtct ccaacgcatc cggcc                                 35
```

-continued

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
cggaaccgaa ctataccacc gagggacgca ttctc                    35

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
atgcctgcag gtcgacgctc aaacgcacga gcgaag                   36

<210> SEQ ID NO 7
<211> LENGTH: 261
<212> TYPE: PRT
<213> ORGANISM: Corynebacterium glutamicum
<220> FEATURE:
<221> NAME/KEY: PEPTIDE
<222> LOCATION: (1)..(261)
<223> OTHER INFORMATION: Esterase encoded by NCgl0717 gene

<400> SEQUENCE: 7

Met Lys Thr Glu Thr Arg Arg Ala Leu Val Phe Ile Val Ala Gly Cys
1               5                   10                  15

Leu Ala Ala Thr Ala Leu Gly Phe Met Val Trp Gln Met Ser Ser Pro
                20                  25                  30

Ser Arg Pro Thr Ser Asp Ile Ala Thr Ser Thr Thr Ser Thr Thr
            35                  40                  45

Gln Thr Gln Ala Arg Tyr Asp Ser Pro Gly Asn Thr Glu Thr Lys Glu
    50                  55                  60

Ala Glu Pro Asp Leu Glu Asn Gln Thr Leu Ala Pro Ile Asn Thr Glu
65                  70                  75                  80

Asp Pro Tyr Leu Pro Pro Asn Ala Phe Val Arg Pro Asp Asn Gly Arg
                85                  90                  95

Ser Ser Gly Leu Thr Pro Ser Gly Ser Ser Pro Thr Thr Thr Ser Arg
            100                 105                 110

Val Ser Ser Pro Ser Ser Ala Gly Ser Ala Ser Pro Thr Gln Ile Thr
        115                 120                 125

Ser Arg Ser Asn Glu Pro Ser Glu Pro Gly Asp Glu Ser Thr Ala Ala
    130                 135                 140

Thr Gln Pro Ser Ser Pro Asp Arg Pro Thr Glu Pro Thr Asn Pro Val
145                 150                 155                 160

Asp Pro Thr Gly Pro Ser Glu Pro Thr Glu Pro Thr Asp Pro Ile Glu
                165                 170                 175

Thr Thr Asp Pro Ile Glu Thr Thr Asp Pro Val Ala Pro Ser Thr Pro
            180                 185                 190

Pro Thr Ser Asp Asp Ser Thr Ser Thr Pro Gln Pro Asp Glu Ser Asp
        195                 200                 205

Thr Pro Pro Thr Asp Phe Val Glu Glu Pro Thr Ala Pro Leu Asn Pro
    210                 215                 220

Asp Gln Pro Ala Gly Ser Thr Thr Asp Ala Thr Pro Asn Ala Thr Pro
225                 230                 235                 240

Ser Ala Pro Ala Asp Thr Thr Ser Asn Ser Val Ala Asn Ser Val Glu
            245                 250                 255

Pro Thr Ala Thr Ser
            260

<210> SEQ ID NO 8
<211> LENGTH: 786
<212> TYPE: DNA
<213> ORGANISM: Corynebacterium glutamicum
<220> FEATURE:
<221> NAME/KEY: gene
<222> LOCATION: (1)..(786)
<223> OTHER INFORMATION: NCgl0717 gene

<400> SEQUENCE: 8
atgaaaacag aaactcgacg agccctcgtc ttcatcgtcg ccggctgttt agccgccacc      60
gccctgggtt ttatggtctg gcagatgtcc agcccaagcc gacccacctc tgatattgcc     120
acgtctacta ctacgtctac cacccaaacc caggctaggt acgattcccc aggtaataca     180
gagaccaaag aggcggaacc tgacctagaa accaaactt tggcgcccat caacaccgaa      240
gatccatatc ttccaccgaa tgcttttgtg cgtccagaca atggccgaag ctccggttta     300
accccttctg gcagttctcc aactaccacc tctcgggtga gttctccctc ctcagcagga     360
tcggcaagcc cgactcaaat cacctccagg tcaaacgagc ctagtgaacc tggtgatgag     420
tcaactgctg ctacacaacc gtcgagccca gacaggccaa ccgaacctac aaatccggta     480
gacccaactg gaccttctga acctacggaa cccaccgatc cgattgagac aaccgatccg     540
attgagacaa ccgatccggt agctccgtcc accccgccaa cgagcgatga ttcaacaagc     600
actccccaac cagatgagtc tgatacgcca cctaccgatt cgtagagga aacctactgct      660 cctctcaatc cggatcagcc agccggttca actactgatg cgacgccaaa cgcaacacca    720
agcgcaccag ctgacacaac atccaattct gtagctaact ctgtggaacc aactgccacg     780
agctaa                                                                786

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
ccggggatcc tctagagttc gcggataaat ggg                                   33

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
cacgtgaaat tcaggtcgcg tggttcacct ccgaag                                36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
cttcggaggt gaaccacgcg acctgaattt cacgtg                              36

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
gcaggtcgac tctagaggtc ccatgattgt tctg                               34

<210> SEQ ID NO 13
<211> LENGTH: 107
<212> TYPE: PRT
<213> ORGANISM: Corynebacterium glutamicum
<220> FEATURE:
<221> NAME/KEY: PEPTIDE
<222> LOCATION: (1)..(107)
<223> OTHER INFORMATION: Esterase encoded by NCgl2912 gene

<400> SEQUENCE: 13

Met Arg Lys Leu Arg Thr Ala Ser Val Ala Leu Leu Thr Ala Gly Ala
1               5                   10                  15

Leu Ala Leu Thr Ala Thr Pro Ala Met Ala Gln Ser Thr Thr Gly Ser
            20                  25                  30

Ser Ala Ser Ser Gln Val Gly Asp Ala Leu Gly Ala Ser Asp Tyr Glu
        35                  40                  45

Arg Asp Ile Trp Gly Ser Ser Lys Asp Phe Asp Val Thr Pro Phe
    50                  55                  60

Gly Ser Ala Trp Tyr Gly Tyr Thr Leu Ala Ala Thr Ala Val Ala Ile
65                  70                  75                  80

Ser Gly Leu Val Tyr Ala Asn Leu Pro Ala Ile Glu Gln Ala Ala Ala
                85                  90                  95

Gln Ala Gly Ile Lys Leu Glu Ile Pro Arg Tyr
            100                 105

<210> SEQ ID NO 14
<211> LENGTH: 324
<212> TYPE: DNA
<213> ORGANISM: Corynebacterium glutamicum
<220> FEATURE:
<221> NAME/KEY: gene
<222> LOCATION: (1)..(324)
<223> OTHER INFORMATION: NCgl2912 gene

<400> SEQUENCE: 14
atgcgtaaac ttcgtactgc ttccgttgca ctgctgaccg caggtgcact tgcactgacc      60
gctactcctg caatggctca gtccaccacc ggttcttctg catcttctca ggttggcgac     120
gcactcggtg ctagcgacta cgagcgcgac atctggggtt cctctaagga cttcgacgat     180
gtaaccccat tcggttccgc ttggtacggc tacaccctgg ccgcaaccgc agttgctatc     240
tccggtcttg tgtacgcaaa ccttcctgca atcgagcagg ctgctgcaca ggccggcatc     300
aagctggaga tcccacgcta ctaa                                           324

<210> SEQ ID NO 15
<211> LENGTH: 33
<212> TYPE: DNA
<213> ORGANISM: Artificial Sequence
<220> FEATURE:

```
<223> OTHER INFORMATION: primer

<400> SEQUENCE: 15
ccggggatcc tctagagctg caagaagtgc gac                              33

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16
ctcgtagtcg ctagcaccta ttacgggagg tc                               32

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
gacctcccgt aataggtgct agcgactacg ag                               32

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
gcaggtcgac tctagacccg agctatctaa cac                              33
```